US006777676B1

(12) United States Patent
Wang et al.

(10) Patent No.: US 6,777,676 B1
(45) Date of Patent: Aug. 17, 2004

(54) NON-DESTRUCTIVE ROOT CAUSE ANALYSIS ON BLOCKED CONTACT OR VIA

(75) Inventors: Ying Wang, San Jose, CA (US);
Yeishin Tung, San Jose, CA (US);
Anne Testoni, Bolton, MA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/303,267

(22) Filed: Nov. 21, 2002

Related U.S. Application Data

(60) Provisional application No. 60/394,411, filed on Jul. 5, 2002.

(51) Int. Cl.[7] .................. G01N 23/00; G01N 21/00; G21K 7/00
(52) U.S. Cl. .................. 250/310; 250/306; 250/307; 378/44; 378/45; 378/48; 257/48; 257/750; 257/754; 438/14; 438/625; 438/672; 356/237.1; 356/241.1; 356/376
(58) Field of Search .................. 250/306, 307, 250/310; 378/44, 45, 48; 257/48, 750, 754; 438/14, 625, 672; 356/237.1, 241.1, 376

(56) References Cited

U.S. PATENT DOCUMENTS

| 3,585,385 | A | * | 6/1971 | Daigne et al. | 250/310 |
|---|---|---|---|---|---|
| 4,439,680 | A | * | 3/1984 | Broadhurst | 250/310 |
| 4,777,364 | A | * | 10/1988 | Sartore | 250/307 |
| 5,877,498 | A | * | 3/1999 | Sugimoto et al. | 250/310 |
| 5,900,645 | A | | 5/1999 | Yamada | 257/48 |
| 6,038,018 | A | | 3/2000 | Yamazaki et al. | 356/237.1 |
| 6,052,429 | A | * | 4/2000 | Ohno et al. | 378/45 |
| 6,351,516 | B1 | | 2/2002 | Mazor et al. | 378/44 |
| 6,476,389 | B1 | * | 11/2002 | Konakawa et al. | 250/310 |
| 6,566,885 | B1 | * | 5/2003 | Pinto et al. | 324/501 |
| 6,576,923 | B2 | * | 6/2003 | Satya et al. | 257/48 |
| 2003/0062477 | A1 | * | 4/2003 | Nasser-Ghodsi et al. | 250/310 |

* cited by examiner

Primary Examiner—John R. Lee
Assistant Examiner—Bernard Souw
(74) Attorney, Agent, or Firm—Beyer Weaver & Thomas

(57) ABSTRACT

Disclosed are apparatus and methods for characterizing a potential defect of a semiconductor structure. A charged particle beam is scanned over a structure which has a potential defect. X-rays are detected from the scanned structure. The X-rays are in response to the charged particle beam being scanned over the structure. The potential defect of the scanned structure is characterized based on the detected X-rays. For example, it may be determined whether a potentially defective via has a $SiO_2$ plug defect by comparing an X-ray count ratio of oxygen over silicon of the defective via with an X-ray count ratio of a known defect-free reference via. If the defective via has a relatively high ratio (more oxygen than silicon) as compared to the reference via, then it may be determined that a $SiO_2$ plug defect is present within the defective via. Otherwise, the via may be defmed as having a different type of defect (e.g., not a $SiO_2$ plug defect) or defined resulting in a "false" defect. Accordingly, specific embodiments of the present invention may be utilized to filter "false" defects from a defect sample.

29 Claims, 8 Drawing Sheets

NON-DESTRUCTIVE ROOT CAUSE ANALYSIS ON BLOCKED CONTACT OR VIA

CROSS REFERENCE TO RELATED APPLICATIONS

This application claims priority of U.S. Provisional Patent Application No. 60/394,411 filed Jul. 5, 2002, which application is. incorporated herein by reference in its entirety for all purposes.

BACKGROUND OF THE INVENTION

The present invention relates generally to systems and methods for characterizing defects on a sample.

Particular types of structures are difficult to analyze. Typically, a plurality of contacts or vias are imaged with a scanning electron microscopy (SEM) inspection tool. An electron beam is scanned across a sample. Secondary and backscattered electrons are emitted from the scanned sample in response to the electron beam. The emitted electrons are detected from the scanned sample to generate an image of the surface, including the contacts or vias. If the contacts or vias are coupled to the same underlying substrate or conductive metal layer, the contacts or vias are expected to have a same intensity of emitted electrons when there are no defects present. Defective contacts or vias are expected to emit a different intensity of electrons than the non-defective vias. As a result of these different intensities, defective contacts or vias have a different intensity or brightness than non-defective contacts or vias within the image generated on an SEM tool. Accordingly, defective contacts or vias may be defined as contacts or vias that have a significantly different intensity than a majority of the scanned contacts or vias or as compared to a known defect-free scanned contacts or via.

There are a number of possible "root causes" for a defective contact or via. For example, two different defect types may have a same appearance during an SEM inspection. Additionally, since contacts or vias have relatively high aspect ratio, they are difficult to image with an SEM system and may result in non-killer or "false" defects during a voltage contrast inspection. In one example, the captured defects may include "killer defects" which are likely to cause a device to fail, as well as non-killer or "false" defects which are not likely to cause a device to fail.

It is also desirable to determine the root cause of a potentially defective contact or via. For example, it is desirable to determine whether the potentially defective contact or via found during the voltage contrast inspection contains a plug defect or is a "false" defect. Currently, this determination is performed by inspecting a cross section of a potentially defective via for a plug defect. A cross section of a defective via is typically obtained using a focused ion beam cross section. The cross section of the contact or via is then imaged with a scanning electron microscopy (SEM) to locate the cause of the defect. In sum, the root cause of a defective contact or via is determined by a focused ion beam cross sectioning and imaging of the potentially defective contact or via. Although this technique succeeds in determining a root cause for a potentially defective via, the sample is destroyed during such technique. This procedure may waste a wafer sample, even though there are only "false" defects present. Additionally, the focused ion beam cross sectioning is time consuming.

Accordingly, there is a need for improved apparatus and methods for efficiently detecting and analyzing potential defects associated with a contact or via and the like.

SUMMARY

In general terms, the present invention provides apparatus and methods for characterizing a potential defect by analyzing the X-ray count(s) of one or more material components (such as the ratio of oxygen over silicon) as emitted from a structure under test in response to electrically charged particles, such as an electron beam scan. For example, it may be determined whether a potentially defective contact or via has a $SiO_2$ plug defect by comparing an X-ray count ratio of oxygen over silicon of the defective via with an X-ray count ratio of a known defect-free reference via. If the defective contact or via has a relatively high ratio (more oxygen than silicon) as compared to the reference contact or via, then it may be determined that a $SiO_2$ plug defect is present within the defective contact or via. Otherwise, the contact or via may be defined as having a different type of defect (e.g., not a $SiO_2$ plug defect) or defined as resulting in a "false" defect. Accordingly, specific embodiments of the present invention may be utilized to filter "false" defects from a defect sample. The X-ray counts of other types of materials may also be analyzed to determine root cause of potential defects, and material selection depends on the particular type of defect being analyzed and structure under test. In other embodiments, the size of a defect may also be determined by analyzing the X-ray counts of one or more materials produced in response to an electron beam scan over a structure under test.

In one embodiment, a method of characterizing a potential defect of a semiconductor structure is disclosed. A charged particle beam is scanned over a structure which has a potential defect. X-rays are detected from the scanned structure. The X-rays are in response to the charged particle beam being scanned over the structure. The potential defect of the scanned structure is characterized based on the detected X-rays.

In a specific implementation, the characterizing operation is based on a ratio of a first X-ray intensity for a first material over a second X-ray intensity for a second material, and the first and second X-ray intensities are obtained from the detected X-rays from the scanned structure. In a further implementation, the scanned structure is a first via or a first contact.

In a further aspect, a charged particle beam is scanned over a reference via. X-rays are detected from the scanned reference via. The X-rays are in response to the charged particle beam being scanned over the reference via. The potential defect is characterized by comparing the first ratio from the scanned first via or contact to a second ratio from the scanned reference via. The second ratio is a third X-ray intensity for the first material over a fourth X-ray intensity for the second material, and the third and fourth X-ray intensities are obtained from the detected X-rays from the scanned reference via In one aspect, the potential defect is located based on the ratio of the first X-ray intensity for the first material over the second X-ray intensity for the second material. In a further aspect, a charged particle beam is scanned over a plurality of second vias or contacts. X-rays are detected from the scanned second vias or contacts, and the X-rays are in response to the charged particle beam being scanned over the second vias or contacts. Characterizing the potential defect of the first via or contact is accomplished by determining whether the first ratio from the scanned first via or contact significantly differs from a majority of second ratios calculated for the second vias. The second ratios of the plurality of vias are each calculated by dividing a third X-ray intensity for the first material by a fourth X-ray intensity for the second material, and the third and fourth X-ray intensities are obtained from the detected X-rays from each of the scanned second vias. In an alternative implementation, the potential defect is located by a voltage contrast inspection of a plurality of vias.

In one implementation, the first and second X-ray intensity are X-ray count values. In a preferred embodiment, the charged particle beam has a spot diameter substantially equal to a diameter of the via. In another aspect, characterizing the potential defect includes determining whether the scanned first via or first contact contains a plug defect, e.g., caused by an under-etching of the via or contact. (A "plug defect" is defined herein as any type of unwanted material which is present within the via or contact). In a further aspect, characterizing the potential defect further includes determining that the potential defect is a real defect when it is determined that the scanned first via or contact contains a plug defect and determining that the potential defect is a false defect when it is determined that the scanned first via or contact does not contain a plug defect. In an alternative further aspect, when it is determined that the first via or contact contains a plug defect, a size of the plug defect is determined based on the ratio of the first X-ray intensity for the first material over the second X-ray intensity for the second material.

In a specific implementation, characterizing the potential defect is accomplished by determining that the potential defect is a plug defect when the ratio is above a predetermined threshold. In an alternative implementation, characterizing the potential defect is accomplished by determining that the potential defect is a plug defect when the ratio is below a predetermined threshold.

In another embodiment, the invention pertains to an apparatus for characterizing a potential defect of a semiconductor structure. The apparatus includes a beam generator operable to direct a charged particle beam towards a structure and a detector positioned to detect X-rays from the structure in response to the charged particle beam. The apparatus further includes a processor arranged to perform one or more of the above described method operations.

These and other features of the present invention will be presented in more detail in the following specification of the invention and the accompanying figures, which illustrate by way of example the principles of the invention.

BRIEF DESCRIPTION OF THE DRAWINGS

The invention, together with further advantages thereof, may best be understood by reference to the following description taken in conjunction with the accompanying drawings.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general terms, X-ray spectral measurement includes analysis of the X-ray region of the electromagnetic spectrum that is associated with a sample so as to gain information regarding the sample. The X-ray region of the electromagnetic spectrum generally includes frequencies that range from about $1.0 \times 10^{17}$ Hz to about $1.0 \times 10^{21}$ Hz although the bounds of this region are not precisely defined. X-ray spectral measurement is performed by bombarding a specimen with electrically charged particles which have sufficient energy to cause X-ray photons to be emitted from the specimen. By counting the emitted photons at one or more energy levels, the composition of conductive layers in a semiconductor device may be determined. The composition of a material may be determined since the specific energy levels of X-ray photons emitted from such material are related to the material's composition.

Figure 1:
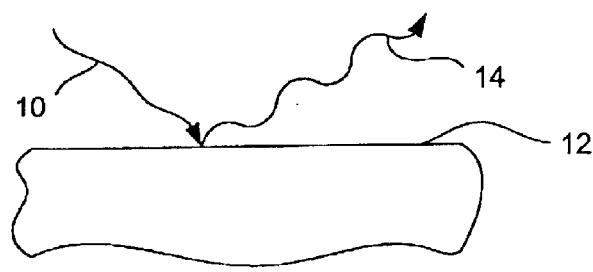
FIG. 1 illustrates an electron beam incident upon a specimen, and a resulting X-ray photon being emitted by the specimen material.
Figure 2A:
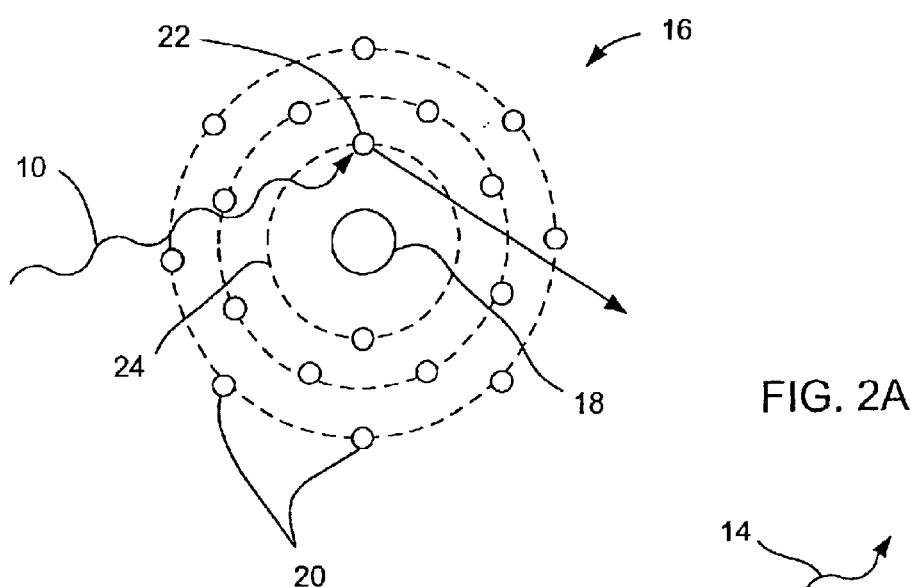
FIG. 2A illustrates the incident electron beam of FIG. 1 impacting an atom of the specimen, and the resulting ejection of an electron the innermost K electron shell of the atom.
Figure 2B:
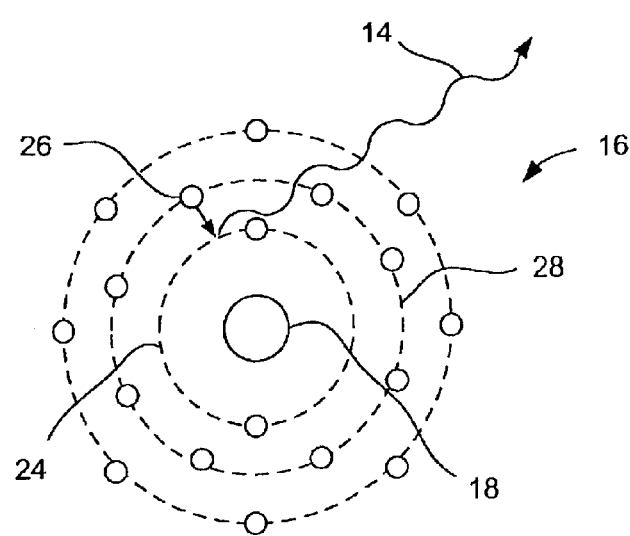
FIG. 2B illustrates an electron in the L electron shell of the atom of the specimen of FIG. 2A filling the vacancy created in the K electron shell, and the simultaneous emission of the secondary X-ray photon.

FIGS. 1, 2A, and 2B illustrate generally how X-ray photons may be caused to emanate from a specimen in accordance with one implementation of the present invention.

FIG. 1 illustrates a charged particle 10, such as an electron, colliding with the surface of a specimen 12. The charged particle 10 may collide with an atom of the specimen 12 and thereby cause an X-ray photon 14 to be emitted from the specimen 12. FIGS. 2A and 2B illustrate this collision event at the atomic level. FIG. 2A shows an atom 16 of the specimen 12. The atom 16 has a nucleus 18 surrounded by electrons 20 at different discrete distances from nucleus 18 called electron shells. A given electron shell has a binding energy level equal to the amount of energy required to remove an electron from the electron shell. The binding energy level of an electron shell is inversely proportional to the distance of the electron shell from the nucleus. The innermost electron shell of an atom is called the K shell, and has the highest binding energy associated with it. In FIG. 2A, K-shell electron 22 is located in K shell 24. The two shells beyond the K shell are the L and M shell, the M shell being the farthest away from the nucleus 18.

FIG. 2A also shows the charged particle 10 impacting atom 16 within the specimen 12. If the energy level of the particle 10 is greater than the binding energy level of a K-shell 24, the entire energy of the particle 10 is absorbed by atom 16 and one of the electrons in K shell 24 is ejected from the atom 16. As depicted in FIG. 2A, K-shell electron 22 is ejected from atom 16 after particle 10 is absorbed by atom 16.

With a vacancy in K shell 24, atom 16 is energetic and unstable. The most probable stabilization mechanism is the filling of the vacancy in K shell 24 by an electron located in an electron shell with a lower binding energy level. As shown in FIG. 2B, an L-shell electron 26 in L shell 28, which is farther from nucleus 18 than K shell 24, may fill the vacancy in. K shell 24. As L-shell electron 26 fills the vacancy in K shell 24, atom 16 may simultaneously emit an X-ray photon 14 with energy ($N_K$–$N_L$), where $N_K$ and $N_L$ are the binding energy levels of K and L shell, respectively. With a vacancy now in L shell 28, ionized atom 16 is more stable and less energetic.

The above described X-ray emission theory may be utilized to determine the composition of materials deposed on a sample since X-ray emissions from the material depend on the material's composition. That is, each material type has an associated atomic shell arrangement. Additionally, the binding energy level for each shell varies with material type. For example, a first material type emits X-rays at energy levels that differ from energy levels of a second material type. In other words, each material type has associated X-ray energy peaks at which X-rays are expected to be emitted. Thus, an unknown material's composition may be determined by comparing the unknown material's X-ray energy peaks with a known material's energy peaks. When a match is found, the unknown material is identified as having the same composition as the matching material.

When the unknown material is formed from two or more elements or components, X-rays detected from the unknown material have energy peaks corresponding to multiple elements. For example, when the unknown material is composed of $SiO_2$, the unknown material has energy peaks matching the energy peaks of both oxygen and silicon. One may also determine an X-ray count ratio of two material components for a particular scanned area of a sample. For instance, the ratio of oxygen over silicon may be determined by dividing the X-ray counts associated with the oxygen peaks by the counts associated with the silicon peaks from a particular area of the unknown material.

In a preferred embodiment, the present invention provides techniques for characterizing a defect by analyzing one or more X-ray count ratios of material components (such as the ratio of oxygen over silicon) as described further below. For example, it may be determined whether a potentially defective contacts or via has a defective $SiO_2$ plug, particle or flake therein by comparing an X-ray count ratio of oxygen over silicon of the defective via with an X-ray count ratio of a known defect-free reference via. The term "plug defect" is used herein to refer to any type of unwanted material, such as a particle of flake, which is present within the contact or via. If the potentially defective via has a relatively high ratio (more oxygen than silicon) as compared to the reference via, then it may be determined that the potentially defective via is, in fact, defective, and that a $SiO_2$ plug or flake defect is present within such defective contact or via Otherwise, the contact or via under test may be defmed as having a different type of defect (e.g., not a $SiO_2$ plug defect) or defined as resulting in a "false" defect. Accordingly, specific embodiments of the present invention may be utilized to filter "false" defects from a defect sample.

In an alternative embodiment, one may also analyze the X-ray count of a single material to characterize a defect. In this case, a potentially defective via which has a relative high oxygen count as compared to another known defect-free via or a majority of other potentially defective via may be characterized as having a $SiO_2$ plug defect. However, the X-ray count ratio technique is preferred over the absolute X-ray count technique due to fluctuations in detected X-rays which may be cancelled out in a ratio calculation as opposed to an absolute approach.

Although the techniques of the present invention are described as being applied to determining a root cause or defect type of potentially defective contacts or vias, these techniques may be applied to any type of defect or structure for which, defect characterization is needed. Preferably, these techniques are used to determine the presence and characterization of defects which cannot be easily imaged by an SEM or optical inspection system. For instance, the techniques may be used to characterize buried defects, such as physical shorts or killer particles, or in the illustrated embodiment to characterize defects within high aspect ratio structures, such as contacts, vias, and trenches.

Figure 3:
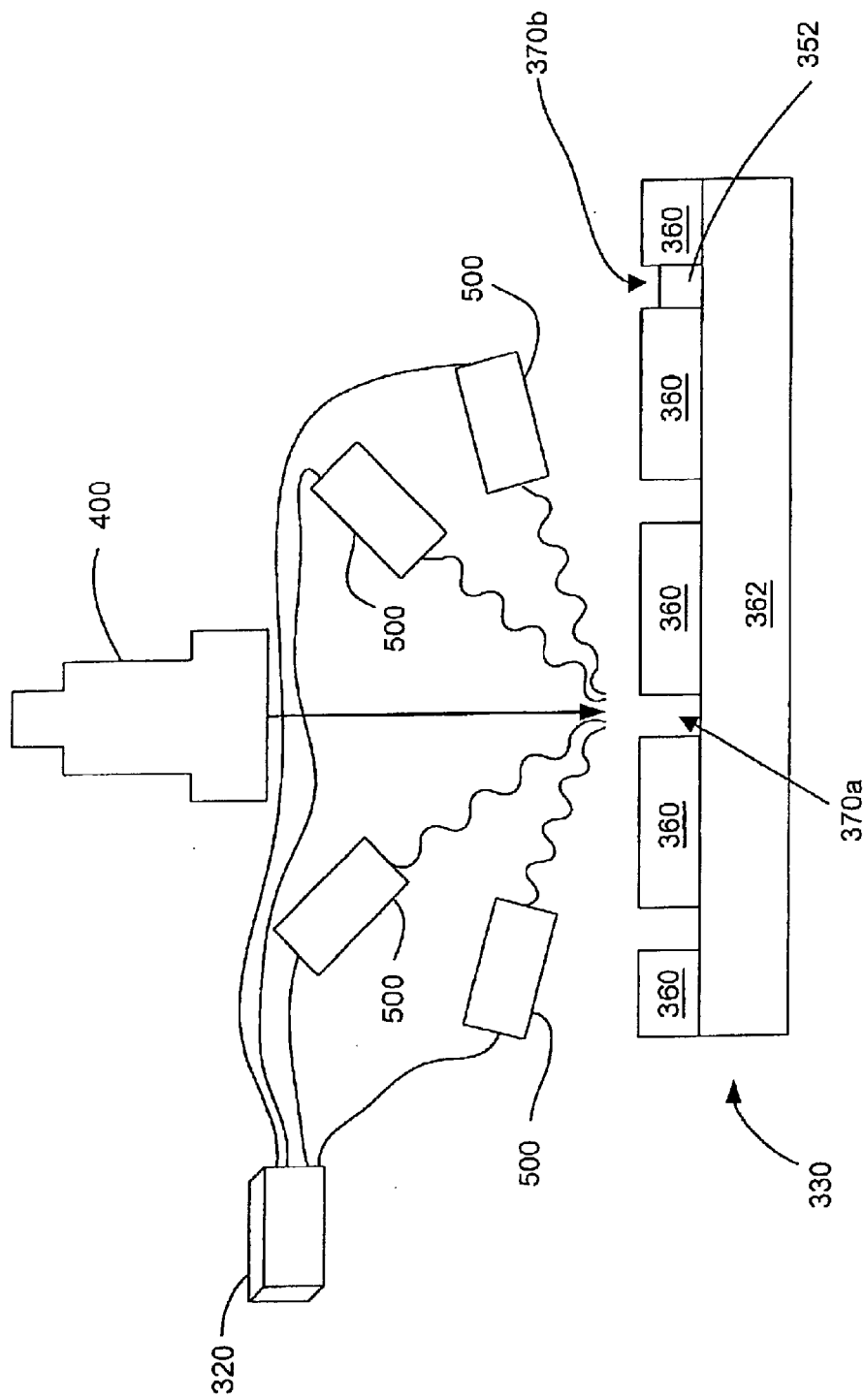
FIG. 3 illustrates an electron beam induced X-ray microanalysis test system according to one embodiment of the present invention.

Any suitable electron beam induced X-ray microanalysis system may be utilized to practice and/or implement the techniques of the present invention. An eV300 automated e-Beam wafer inspection system available from KLA-Tencor Corporation of San Jose, Calif. may be used. FIG. 3 is a diagrammatic representation of a system utilizing an electron beam induced X-ray microanalysis test system according to one embodiment of the present invention. The system represented in FIG. 3 includes a beam generator 400, which directs a charged particle beam at the specimen 330. The spot size of beam scanning may be any suitable size. In one embodiment, the spot diameter of the system corresponds to approximately the diameter of a contact or via. In current processes, a contact or via diameter is approximately 230 nanometers in diameter. The specimen 330 is a multi-layered semiconductor wafer for which defect root cause analysis is desired. X-ray detectors 500 are positioned above the specimen 330 in order to collect the X-ray photons emitted from the specimen 330.

Any suitable number and type of detector for measuring X-rays at specific energy levels may be utilized. One type of detector is an Energy Dispersive System (EDS), which collects photons in a wide spectrum of energies. EDS are capable of collecting a greater range of signals. As a result however, EDS detectors also collect photons having energies surrounding the characteristic photon energies. This causes EDS detectors to have lower signal to noise ratios. Another type of detector is a wavelength dispersive system (WDS) X-ray detector. Several suitable embodiments of WDS X-ray detectors are described further in co-pending U.S. patent application Ser. No. 09/695,726, filed Oct. 23, 2000, which application is incorporated herein in its entirety.

Each of the X-ray detectors are coupled with an analysis or processor unit 320. The analysis unit 320 can be configured to analyze the data collected by the X-ray detectors 500 and to generate useful information concerning the ratios of particular material components within multiple scan areas. The analysis unit 320 may take the form of any suitable processing or computing system, such as a workstation. The analysis/processor unit 320 may also be operable to control various operating conditions of the system. By way of examples, the processor unit 320 may be operable to calibrate the following operating conditions so as to accurately determine root cause of a particular type of potentially defective structure, as explained further below: landing energy of the charged particle beam, current of the charged particle beam, and degree of stage tilt upon which the sample is held.

The beam generator 400 may be any suitable device that directs charged particles towards a specimen, and which, in turn, causes X-rays to emanate from the sample under test. The generator 400 is capable of projecting the charged particles with sufficient energy to penetrate at least the depth of both a non-defective via and a defective via. By way of example, the generator is operable to penetrate a defective via that is completely filled with a dielectric plug and has a depth of 1 μm and diameter of 230 nm. A charged particle beam having a landing energy of about 5 kV works well for this depth. Preferably, the particles penetrate substantially through a via filled with a conductive plug, such as tungsten or copper, so as to cause X-rays to emanate from the entire width of the plug. Heavier conductive materials may require a higher landing energy, e.g., 10 kV. As a result, X-ray measurements from the entire thickness of the penetrated plug may then be taken so as to determine whether the conductive plug also contains a dielectric flake or plug type defect. The stage tilt may also be varied so as to detect X-rays from various angles of the via, such as from the sidewalls as opposed to the bottom of the via.

Figure 4:
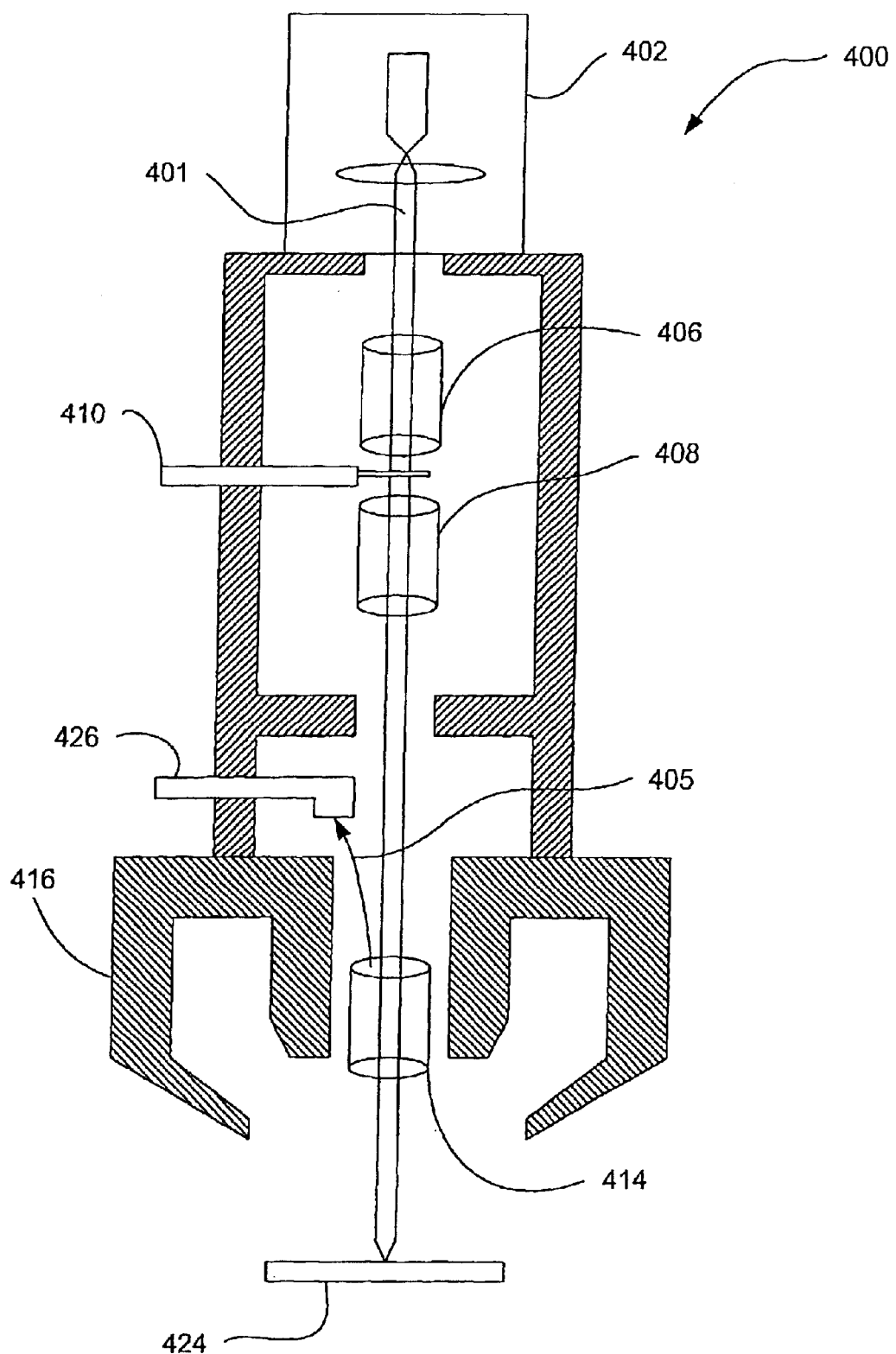
FIG. 4 illustrates a typical scanning electron microscope in accordance with one embodiment of the present invention.

By way of example, the beam generator 400 may take the form of a scanning electron microscope (SEM). FIG. 4 is a diagrammatic representation of a typical scanning electron microscope (SEM) system 400. As shown, the SEM system 400 includes an electron beam generator (402 through 416) that generates and directs an electron beam 401 substantially toward an area of interest on a specimen 424. The SEM system 400 may also include a detector 426 arranged to detect charged particles 405 (secondary electrons, and/or backscattered electrons) emitted from the specimen 424.

As shown, the electron beam generator includes an electron source unit 402, an alignment octupole 406, an electrostatic predeflector 408, a variable aperture 410, a wien filter 414, and a magnetic objective lens 416. The source unit 402 may be implemented in any suitable form for generating and emitting electrons. For example, the source unit 402 may be in the form of a filament that is heated such that electrons within the filament are excited and emitted from the filament. The octupole 406 is configured to align the beam after a particular gun lens voltage is selected. In other words, the beam may have to be moved such that it is realigned with respect to the aperture 410.

The aperture 410 forms a hole through which the beam is directed. The lower quadrupole 408 may be included to compensate for mechanical alignment discrepancies. That is, the lower quadrupole 408 is used to adjust the alignment of the beam with respect to any misaligned through-holes of the SEM through which the beam must travel. The magnetic objective lens 416 provides a mechanism for accelerating the beam towards the sample. Finally, the Wien filter 414 deflects secondary electrons towards the detector 426.

The specimen or sample 330 may take a variety of forms for which X-ray count ratios are desired. In the illustrated embodiment, the specimen 330 is a semiconductor wafer having a silicon substrate 362 upon which a dielectric layer 360 is patterned. As shown, dielectric layer 360 includes a plurality of vias, e.g., 370*a* and 370*b*. Via 370*b* has a defective dielectric plug 352 (e.g., $SiO_2$), while via 370*a* does not have such a defect. As described further below, the X-ray count ratio of oxygen over silicon of a defective via 370*b* may be compared to the ratio of the non-defective via 370*a* to detect the presence of the defective dielectric plug 352. In other embodiments, the vias under review are formed through a dielectric layer disposed on a conductive layer, such as copper, a copper alloy, aluminum, an aluminum alloy, or tungsten.

Figure 5A:
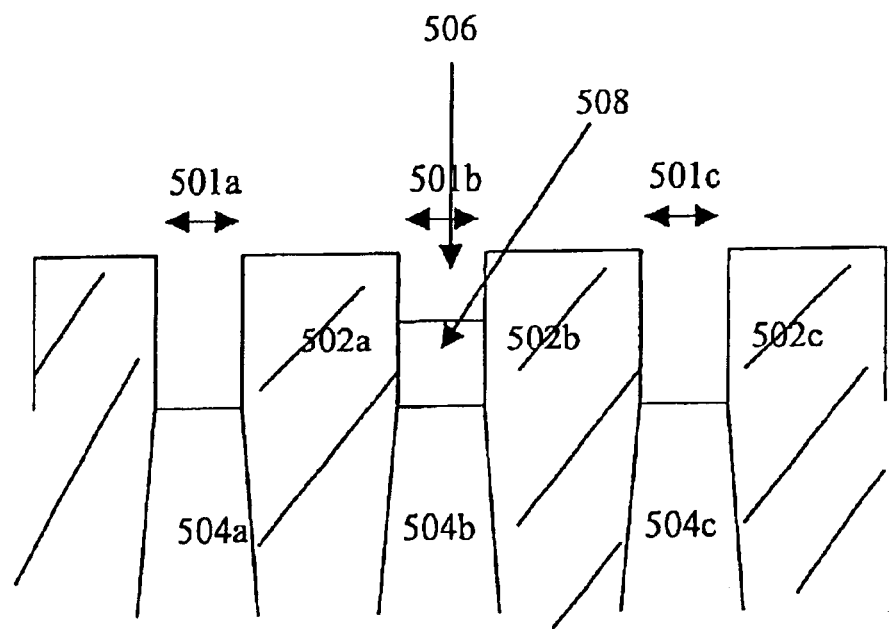
FIGS. 5A and 5B illustrate cross sectional views of two contact or via structures on which the techniques of the present invention may be implemented
Figure 5B:
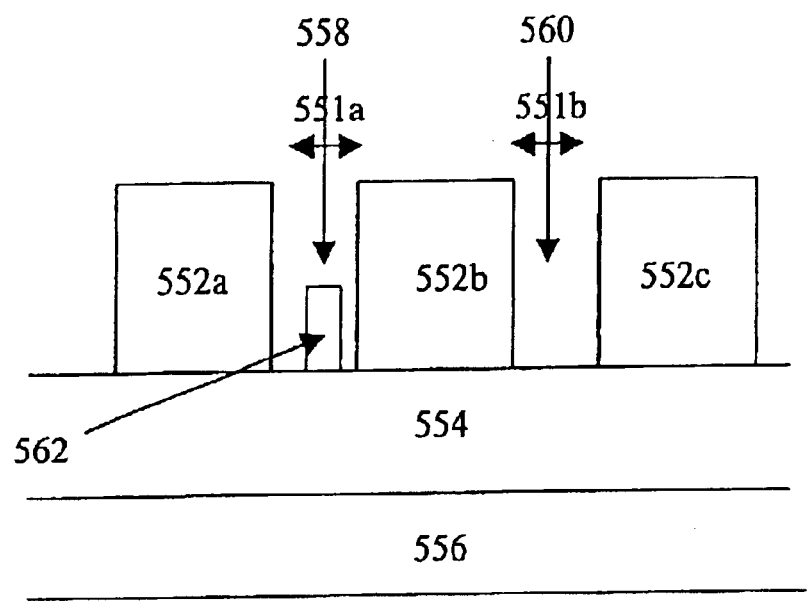

The vias under examination may be any suitable shape and composition. Additionally, the vias may be formed from materials which are the same or different than the material composition of the defect. FIGS. 5A and 5B illustrate cross sectional views of two via structures on which the techniques of the present invention may be implemented. As shown in FIG. 5A, a plurality of vias 501 are formed within a first material 502, such as a dielectric material. Each via 501 contains a second material 504, such as a conductive material. Typically, the second material 504 within each via 510 is coupled to portions of an underlying conductive layer or substrate (not shown). The via 501*b* contains a defect 508, while the other vias 501*a* and 501*c* do not contain a defect. The defect may be any kind of defect which blocks conduction through the via. For example, the defect 508 may be in the form of a dielectric plug, such as a $SiO_2$ plug, that completely or partially fills the defective via 501*b*. In this case, the dielectric plug would block conduction between an upper conductive layer portion (not shown) and the underlying conductive portion 504*b*. Each via may also be filled with a conductive material or plug, such as copper, which may or may not itself contain a dielectric flake or plug type defect therein.

The first and second materials 502 and 504 may be formed from any two different material types. One general type of materials include conductive materials, such as copper, copper alloys, aluminum, aluminum alloys, tungsten, tungsten alloys, polysilicon or other gate materials. Another general category of materials include dielectric or insulating materials, such as $SiO_2$, BPSG, FSG, OSG and any other types of low k dielectric. Another group of materials includes semiconductor materials, such as silicon and gallium arsenide. The structure of FIG. 5A may represent, for example, dielectric vias 501 which are partially filled with conductive plugs 504.

Other example via structures are shown in FIG. 5B. As shown, a first material 552 is deposited over a second material 554. The second material is deposited over a third material 556. The first material is patterned to have a plurality of vias or contacts 551. The first, second, and third materials are different materials and may each be formed from any type of material. In a typical example, the first material 552 is a dielectric material; the second material 554 is a conductive material, and the third material 556 is a dielectric material or substrate. The via 551*a* contains defect 562, while via 551*b* does not contain a defect. As illustrated in FIG. 5B, the defect 562 may only partially fill a diameter of the is via 551*a*. In contrast, the defect may completely cover the diameter of the via as shown in FIG. 5A. The defect may also partially or completely fill the via along the via's depth. For instance, the defect may completely fill the via along its entire depth. In sum, the defect may have any size or shape.

Figure 6:
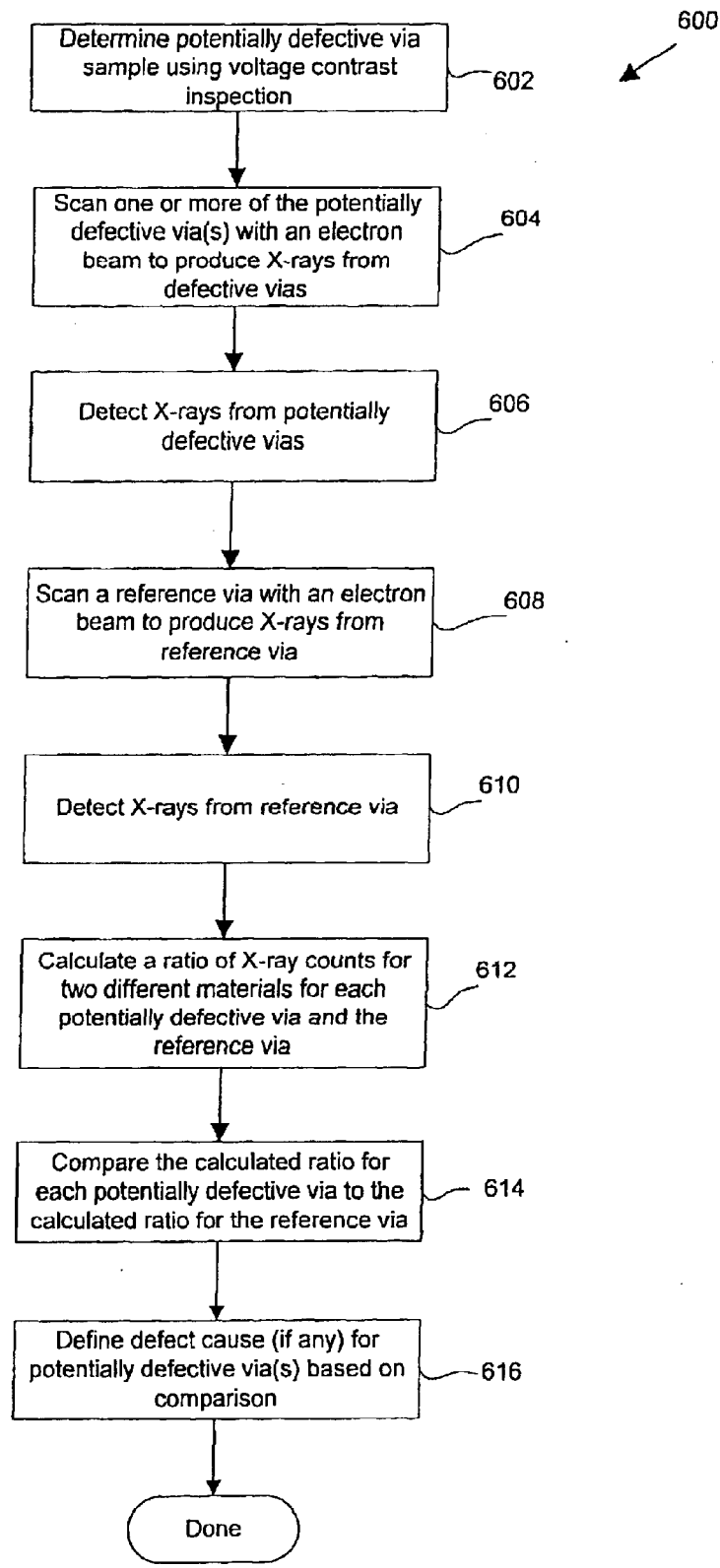
FIG. 6 is a flowchart illustrating a procedure for determining a root cause of a potential defect of a contact or via structure in accordance with one embodiment of the present invention.

FIG. 6 is a flowchart illustrating a procedure 600 for determining a root cause of a potential defect of a via structure in accordance with one embodiment of the present invention. Initially, a potentially defective via sample is found using voltage contrast inspection in operation 602. Any suitable inspection system may be used, such as an eS20 e-Beam review tool by KLA-Tencor Corporation of San Jose, Calif.

Figure 7:
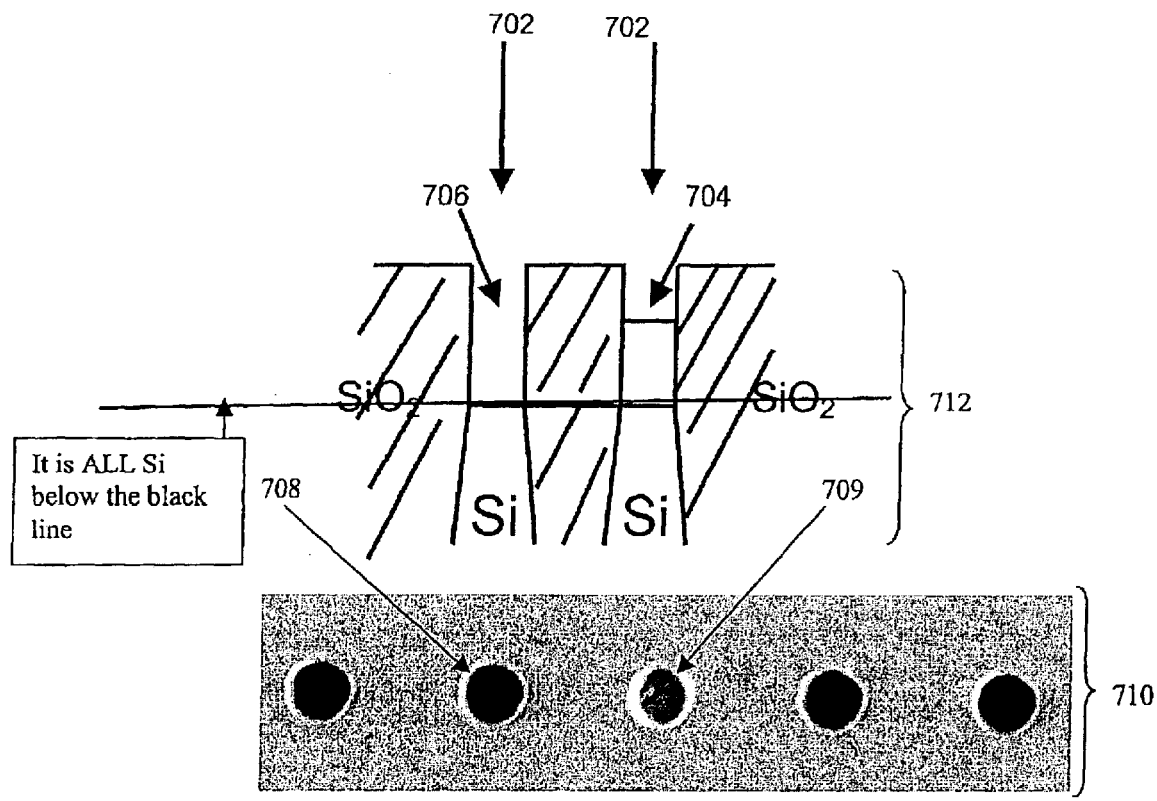
FIG. 7 is a diagrammatic representation of a structure being inspected by a voltage contrast technique and its resulting image.

FIG. 7 is a diagrammatic representation of a structure 712 being inspected by a voltage contrast technique and its resulting image 710. In one voltage contrast technique, a plurality of vias (e.g., 704 and 706) are scanned with an electron beam 702. The secondary and backscattered electrons from the scanned vias are used to form image 712 of the scanned vias. Alternatively, an intensity signal may be produced. The vias may be expected to produce a particular pattern of intensity values (e.g., bright and light patterns) when there is no defect present. Different electron intensity values are produced because the vias are typically designed to produce a particular voltage potential when scanned with an electron beam. For example, the bottom of each via may be formed from a conductive or substrate material, while the vias are formed in a dielectric material. Thus, when the vias and surrounding dielectric material are scanned by an electron beam, the vias appear dark (e.g., 708) while the surrounding dielectric material appears bright. When a via is defective, it likely results in a different intensity than when it is not defective. For example, a defective via appears bright (e.g., 708) and a defect-free via appears dark (e.g., 709), or visa versa. Accordingly, one or more potentially defective via(s) are defined using a "voltage contrast" technique. These potentially defective via(s) are then used to form a sample which are then reviewed to characterize the defects of the via(s).

Referring back to FIG. 6, one or more potentially defective via(s) from the sample are then scanned with an electron beam to produce X-rays from the potentially defective via(s) in operation 604. X-rays are then detected from the potentially defective via(s) in operation 606. In one implementation, the electron beam is scanned over an area that only includes a single via or contact so that X-rays that are detected are known to originate only from the scanned via or contact. For example, a first via area is scanned with the electron beam, and X-rays are then detected from the scanned first via area. A second via area is then scanned with the electron beam, and X-rays are then detected from the scanned second via area Alternatively, a wide electron beam or multiple electron beams may simultaneously scan a group of vias or contacts. The X-rays from each scanned via or contact may be distinguished by calculating the ratios of X-ray counts for two different materials (or an absolute X-ray count) at each via position. That is, the X-ray ratios (or counts) are correlated with via coordinates on the sample. The X-ray ratio (or absolute X-ray count) for each via is then compared to the other vias or to a reference via to determine which via has a plug defect. For example, a via with a significantly different X-ray ratio (or absolute count) is determined to have a plug defect, similar to the techniques described above.

A reference via may then be scanned with an electron beam to produce X-rays from the reference via in operation 608. A reference via is generally defined as a via that is known to be defect-free. X-rays may then be detected from the reference via in operation 610. A ratio of X-ray counts for two different materials for each defective via and the reference via is then calculated in operation 612. For the vias of FIG. 5A, a ratio of material 504 over material 502 (or material 502 over material 504) may be calculated for each via. For the vias of FIG. 5B, a ratio of material 554 over material 552 (or material 552 over material 554) may be calculated for each via. In other words, a ratio of the material that is expected to be at the bottom of each via over the material that is expected to be in each sidewall over the material that is expected to be at the bottom of each via is calculated. Alternatively, the ratio of two materials that may be present within a particular type of defect may be calculated. For instance, a ratio of oxygen over silicon may be calculated to determine whether the via is filled with a $SiO_2$ defect material. Any suitable material types may be used to calculate the ratio which corresponds to a particular defect type.

Referring back to FIG. 6, the calculated ratio for each potentially defective via is then compared to the calculated ratio for the reference via in operation 614. A defect cause may then be defined for the defective via(s) based on the comparison in operation 616. In one embodiment, a ratio is calculated by dividing an X-ray count for material that would be at the bottom of a defect-free via by an X-ray count of material of the side wall material of such defect-free material. Vias which contain defect plugs will have a significantly different ratio than the reference via since the bottom surface of the defective via is at least partially covered by a defect plug. Accordingly, the ratio or intensity of characteristic X-ray lines of potentially defective vias is significantly different from that of good vias. The procedure. 600 then ends. In another embodiment, a ratio of oxygen over silicon is calculated for the potentially defective and reference vias. The potentially defective vias which have a significantly higher ratio may be determined to have $SiO_2$ plug defects. Alternatively, a ratio of silicon over oxygen may be calculated. For this case, those potentially defective vias which have a significantly lower ratio may be defined as having $SiO_2$ plug defects.

Figure 8:
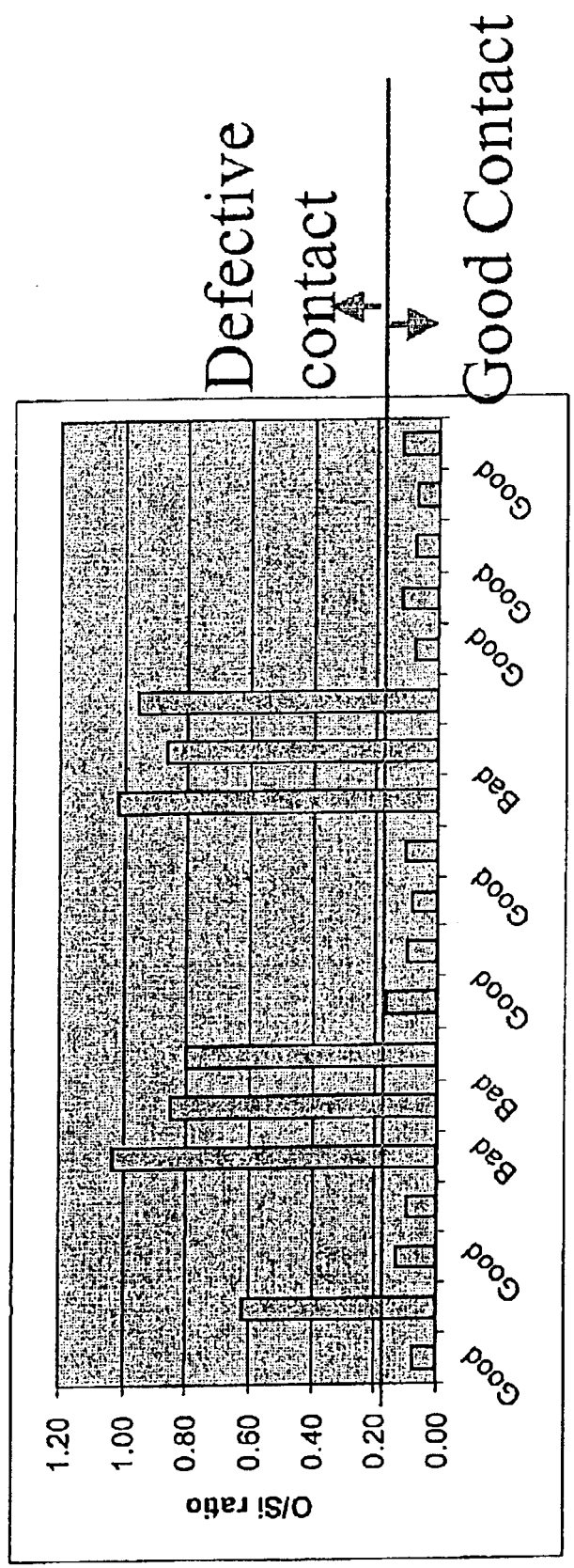
FIG. 8 is a bar graph of ratio values for a plurality of potentially defective contacts in accordance with one embodiment of the present invention.

FIG. 8 is a bar graph of ratio values for a plurality of potentially defective vias in accordance with one embodiment of the present invention. In this example, each ratio is calculated by dividing an X-ray count for oxygen by an X-ray count for silicon. Vias which have a significantly high ratio value may be defined as having $SiO_2$ plug defects. That is, a predefined threshold value may be selected such that vias with ratios higher (or alternatively lower) than the predefined threshold may be defined to have a particular defect, such as a $SiO_2$ plug defect. As shown, vias which have a ratio greater than about 0.18 are defined as having a $SiO_2$ plug defect. Vias which have a ratio value lower than about 0.18 may be defined as "false" defects or as having a different type of defect, e.g., as not having a $SiO_2$ plug defect. In another embodiment, one of the scanned vias may be a reference via which is known to be defect free. Any scanned via which has a ratio that is significantly different than the scanned reference via's ratio may then be defined as having a particular type of defect, such as a plug defect.

Figure 9:
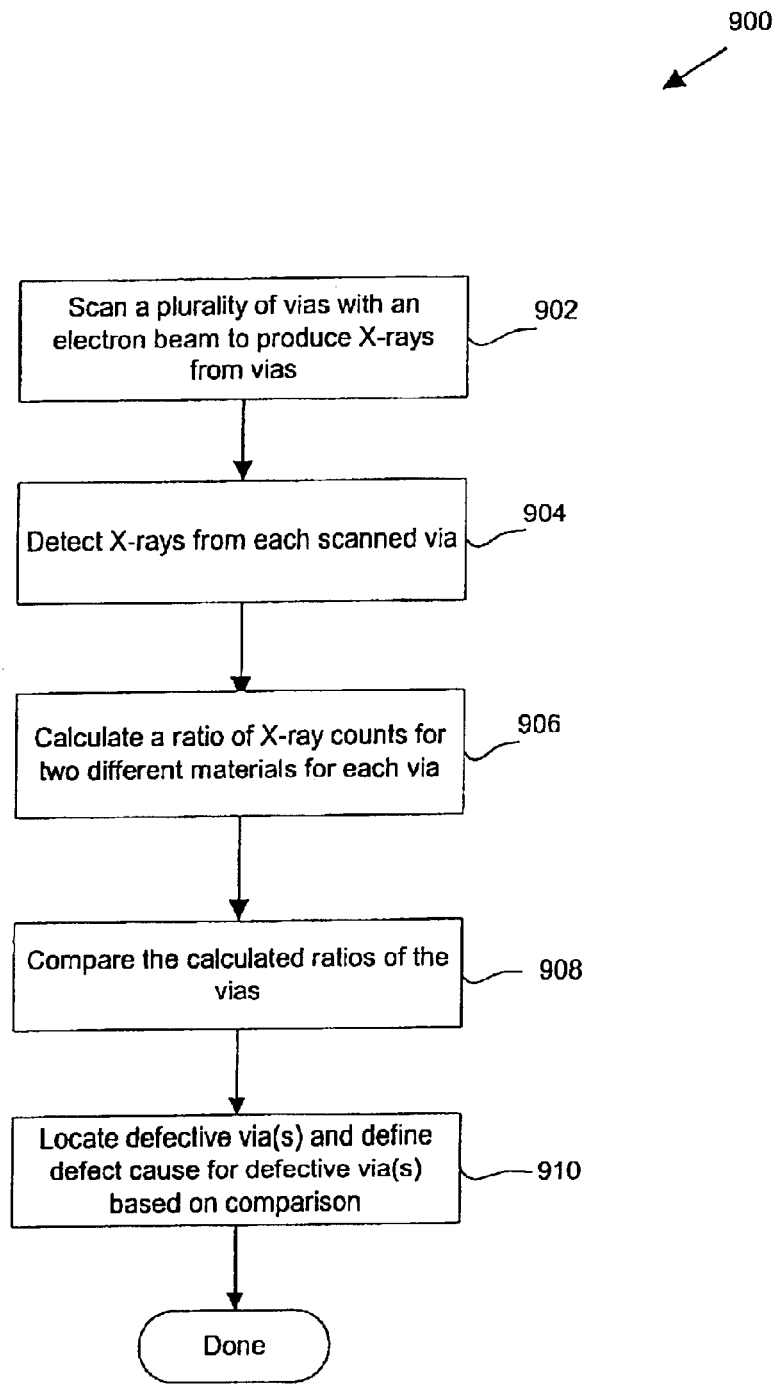
FIG. 9 is a flowchart illustrating an alternative procedure for locating defective contacts or vias and defining a root cause for such defective contacts or vias in accordance with one alternative embodiment of the present invention.

As described above, defects may first be located by a voltage contrast inspection and then defined using X-ray microanalysis. Alternatively, defects may be both located and defined using X-ray microanalysis. FIG. 9 is a flowchart illustrating an alternative procedure 900 for locating defective vias and defining a root cause for such defective vias in accordance with one alternative embodiment of the present invention. Initially, a plurality of vias are scanned with an electron beam to produce X-rays from the vias in operation 902. X-rays are then detected from each scanned via in operation 904. A ratio of X-ray counts for two different materials is then calculated for each via in operation 906.

The calculated ratios of a defective via are then compared in operation 908. In an alternative embodiment, absolute X-ray count values for a single material may be compared.

Defective vias are then located and defect causes are defined for the defective vias based on the comparison in operation 910. In one embodiment, one of the scanned vias may include a known defect-free reference via. The ratios of the other scanned vias may then be compared with the ratio of the scanned reference via using techniques described above to determine whether any of the scanned vias have a particular type of defect, such as a plug defect. In another embodiment, the scanned vias do not include a reference via. In this case, the ratios are compared to each other and any significantly different ratio value may be defined as a particular defect type. The procedure 900 then ends.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A method of characterizing a potential defect of a semiconductor structure, comprising:

scanning a charged particle beam over a structure which has a potential defect;

detecting X-rays from the scanned structure, the X-rays being in response to the charged particle beam being scanned over the structure; and characterizing the potential defect of the scanned structure based on the detected X-rays, wherein the characterizing operation is based on a ratio of a first X-ray intensity for a first material over a second X-ray intensity for a second material and the first and second X-ray intensities are obtained from the detected X-rays from the scanned structure, wherein the potential defect is characterized by comparing the ratio of the first X-ray intensity with one or more reference ratios.

2. A method as recited in claim 1, wherein the first X-ray intensity occurs at a first energy level that corresponds to the first material and the second X-ray intensity occurs at a second energy level that corresponds to a second material.

3. A method as recited in claim 2, wherein the scanned structure is a first via or a first contact.

4. A method as recited in claim 3, further comprising:

scanning a charged particle beam over a reference via; and detecting X-rays from the scanned reference via, the X-rays being in response to the charged particle beam being scanned over the reference via, wherein the potential defect is characterized by comparing the first ratio from the scanned first via or contact to a second ratio from the scanned reference via, wherein the second ratio is a third X-ray intensity for the first material over a fourth X-ray intensity for the second material, wherein the third and fourth X-ray intensities are obtained from the detected X-rays from the scanned reference via.

5. A method as recited in claim 3, further comprising locating the potential defect based on the ratio of the first X-ray intensity for the first material over the second X-ray intensity for the second material.

6. A method as recited in claim 5, further comprising:

scanning a charged particle beam over a plurality of second vias or contacts; and detecting X-rays from the scanned second vias or contacts, the X-rays being in response to the charged particle beam being scanned over the second vias or contacts, wherein characterizing the potential defect of the first via or contact is accomplished by determining whether the first ratio from the scanned first via or contact significantly differs from a majority of second ratios calculated for the second vias, wherein the second ratios of the plurality of vias are each calculated by dividing a third X-ray intensity for the first material by a fourth X-ray intensity for the second material, wherein the third and fourth X-ray intensities are obtained from the detected X-rays from each of the scanned second vias.

7. A method as recited in claim 3, further comprising locating the potential defect by a voltage contrast inspection of a plurality of vias.

8. A method as recited in claim 3, wherein the first and second X-ray intensity are X-ray count values.

9. A method as recited in claim 3, wherein the charged particle beam has a spot diameter substantially equal to a diameter of the via.

10. A method as recited in claim 3, wherein characterizing the potential defect includes determining whether the scanned first via or first contact contains a plug defect.

11. A method as recited in claim 10, wherein characterizing the potential defect further includes determining that the potential defect is a real defect when it is determined that the scanned first via or contact contains a plug defect and determining that the potential defect is a false defect when it is determined that the scanned first via or contact does not contain a plug defect.

12. A method as recited in claim 10, further comprising when it is determined that the first via or contact contains a plug defect, determining a size of the plug defect based on the ratio of the first X-ray intensity for the first material over the second X-ray intensity for the second material.

13. A method as recited in claim 3, wherein the first material is oxygen or silicon and the second material differs from the first material and is either oxygen or silicon.

14. A method as recited in claim 3, wherein the first material is dielectric material or a conductive material and the second material differs from the first material and is either a dielectric material or a conductive material.

15. A method as recited in claim 3, wherein characterizing the potential defect is accomplished by determining that the potential defect is a plug defect when the ratio is above a predetermined threshold.

16. A method as recited in claim 3, wherein characterizing the potential defect is accomplished by determining that the potential defect is a plug defect when the ratio is below a predetermined threshold.

17. An apparatus for characterizing a potential defect of a semiconductor structure, comprising:

a beam generator operable to direct a charged particle beam towards a structure;

a detector positioned to detect X-rays from the structure in response to the charged particle beam; and a processor operable to:

cause the beam generator to direct a charged particle beam towards the structure; and characterize the potential defect of the scanned structure based on the detected X-rays, wherein the characterizing operation is based on a ratio of a first X-ray intensity for a first material over a second X-ray intensity for a second material and the first and second X-ray intensities are obtained from the detected X-rays from the scanned structure, wherein the potential defect is characterized by comparing the ratio of the first X-ray intensity with one or more reference ratios.

18. An apparatus as recited in claim 17, wherein the first X-ray intensity occurs at a first energy level that corresponds to the first material and the second X-ray intensity occurs at a second energy level that corresponds to a second material.

19. An apparatus as recited in claim 18, wherein the scanned structure is a first via or a first contact.

20. An apparatus as recited in claim 19, wherein the processor is further operable to:
cause the beam generator to scan a charged particle beam over a reference via, and
wherein the potential defect is characterized by comparing the first ratio from the scanned first via or contact to a second ratio from the scanned reference via, wherein the second ratio is a third X-ray intensity for the first material over a fourth X-ray intensity for the second material, wherein the third and fourth X-ray intensities are obtained from X-rays detected from the scanned reference via.

21. An apparatus as recited in claim 19, wherein the processor is further operable to locate the potential defect based on the ratio of the first X-ray intensity for the first material over the second X-ray intensity for the second material.

22. An apparatus as recited in claim 21, wherein the processor is further operable to:
cause the beam generator to scan a charged particle beam over a plurality of second vias or contacts, and
wherein characterizing the potential defect of the first via or contact is accomplished by determining whether the first ratio from the scanned first via or contact significantly differs from a majority of second ratios calculated for the second vias, wherein the second ratios of the plurality of vias are each calculated by dividing a third X-ray intensity for the first material by a fourth X-ray intensity for the second material, wherein the third and fourth X-ray intensities are obtained from X-rays detected from each of the scanned second vias.

23. An apparatus as recited in claim 19, wherein the first and second X-ray intensity are X-ray count values.

24. An apparatus as recited in claim 19, wherein the charged particle beam has a spot diameter substantially equal to a diameter of the via.

25. An apparatus as recited in claim 19, wherein characterizing the potential defect includes determining whether the scanned first via or first contact contains a plug defect.

26. An apparatus as recited in claim 25, wherein characterizing the potential defect further includes determining that the potential defect is a real defect when it is determined that the scanned first via or contact contains a plug defect and determining that the potential defect is a false defect when it is determined that the scanned first via or contact does not contain a plug defect.

27. An apparatus as recited in claim 25, wherein the processor is further operable to determine a size of the plug defect based on the ratio of the first X-ray intensity for the first material over the second X-ray intensity for the second material when it is determined that the first via or contact contains a plug defect.

28. An apparatus as recited in claim 19, wherein characterizing the potential defect is accomplished by determining that the potential defect is a plug defect when the ratio is above a predetermined threshold.

29. An apparatus as recited in claim 19, wherein characterizing the potential defect is accomplished by determining that the potential defect is a plug defect when the ratio is below a predetermined threshold.

* * * * *